United States Patent
Koehler et al.

(10) Patent No.: US 9,782,138 B2
(45) Date of Patent: Oct. 10, 2017

(54) IMAGING APPARATUS AND METHOD

(71) Applicant: KONINKLIJKE PHILIPS N.V., Eindhoven (NL)

(72) Inventors: Thomas Koehler, Norderstedt (DE); Roland Proksa, Neu Wulmstorf (DE); Bernhard Johannes Brendel, Norderstedt (DE); Ewald Roessl, Henstedt-Ulzburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/036,521

(22) PCT Filed: Sep. 22, 2015

(86) PCT No.: PCT/EP2015/071734
§ 371 (c)(1),
(2) Date: May 13, 2016

(87) PCT Pub. No.: WO2016/050562
PCT Pub. Date: Apr. 7, 2016

(65) Prior Publication Data
US 2017/0196524 A1   Jul. 13, 2017

(30) Foreign Application Priority Data

Oct. 1, 2014   (EP) .................................... 14187276

(51) Int. Cl.
*A61B 6/00* (2006.01)
*A61B 6/03* (2006.01)
*G21K 1/02* (2006.01)

(52) U.S. Cl.
CPC ............ *A61B 6/4291* (2013.01); *A61B 6/032* (2013.01); *A61B 6/4241* (2013.01); *A61B 6/54* (2013.01); *G21K 1/025* (2013.01)

(58) Field of Classification Search
CPC ........... A61B 6/00; A61B 6/032; A61B 6/035; A61B 6/40; A61B 6/4021; A61B 6/405;
(Continued)

(56) References Cited

U.S. PATENT DOCUMENTS

| | | | |
|---|---|---|---|
| 7,734,017 B2 | 6/2010 | Zeitler et al. | |
| 2009/0161816 A1 | 6/2009 | De Man et al. | |

(Continued)

FOREIGN PATENT DOCUMENTS

| | | |
|---|---|---|
| JP | 5256950 | 10/1993 |
| JP | 11253435 | 9/1999 |

(Continued)

OTHER PUBLICATIONS

Hseih, et al., "The piecewise-linear dynamic attenuator reduces the impact of count rate loss with photon-counting detectors", Phys Med Biol. Jun. 7, 2014; 59(11): 2829-2847.

*Primary Examiner* — Jurie Yun

(57) ABSTRACT

An imaging apparatus comprising a radiation source (2) for emitting radiation from a focal region (20) through an imaging area (5), a detection unit (6) for detecting radiation from said imaging area (5), said detection unit comprising an anti-scatter grid (62) and a detector (61), a gantry (1) to which said radiation source (2) and said detection unit (6) are mounted and a controller (9) for controlling said detection unit (6) to detect radiation at a plurality of projection positions and for manipulating the position, setting and/or orientation of at least a part of said radiation source (2) and/or said detection unit (6) at first projection positions (80) so that the radiation incident on the detector (61) at said first projection positions is attenuated by said anti-scatter grid (62) to a larger extent compared to second projection positions (80) representing the remaining projection positions.

15 Claims, 5 Drawing Sheets

(58) Field of Classification Search
CPC ........... A61B 6/54; A61B 6/542; A61B 6/544; A61B 6/06; H05G 1/30; H05G 1/58; G21K 1/02; G21K 1/04
USPC ............ 378/4, 11, 15, 16, 19, 114, 145, 154
See application file for complete search history.

(56) References Cited

U.S. PATENT DOCUMENTS

| | | |
|---|---|---|
| 2011/0064190 A1 | 3/2011 | Ruimi et al. |
| 2011/0176663 A1 | 7/2011 | Shaughnessy |

FOREIGN PATENT DOCUMENTS

| | | |
|---|---|---|
| JP | 11295430 | 10/1999 |
| JP | 2012034745 | 2/2012 |
| JP | 2012152304 | 8/2012 |
| JP | 2013040859 | 2/2013 |
| WO | 2010/133920 | 11/2010 |
| WO | 2013/093726 | 6/2013 |
| WO | 2013/182928 | 12/2013 |

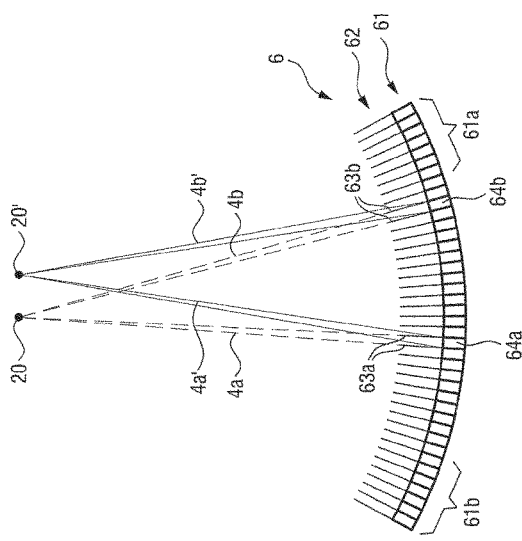
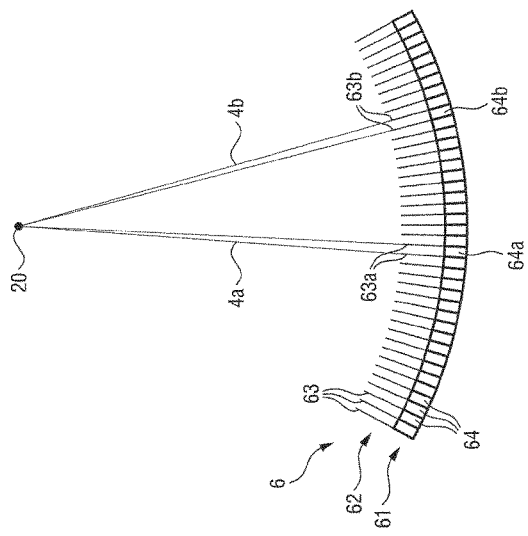

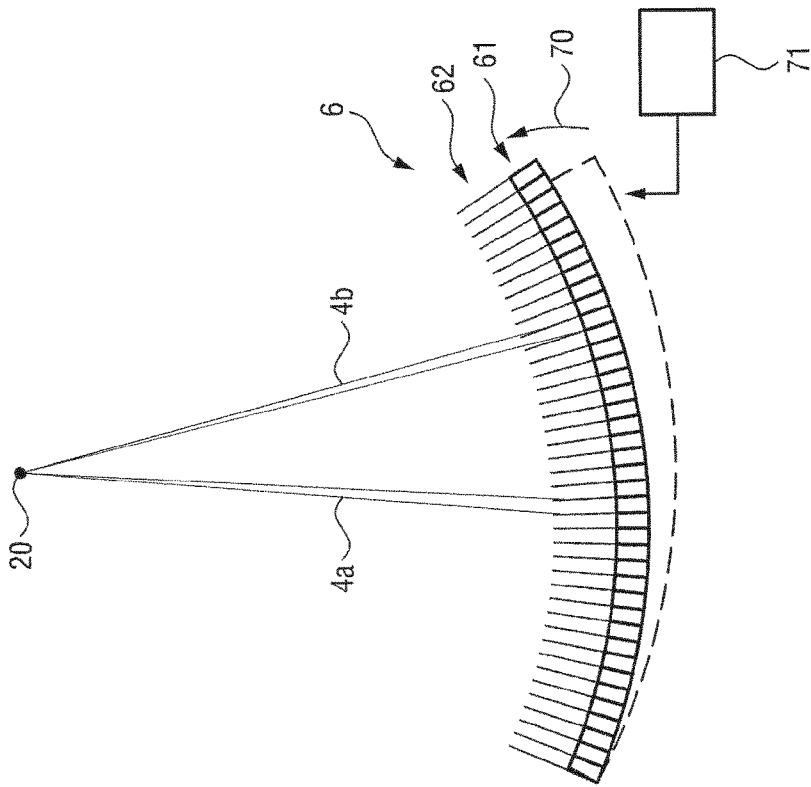
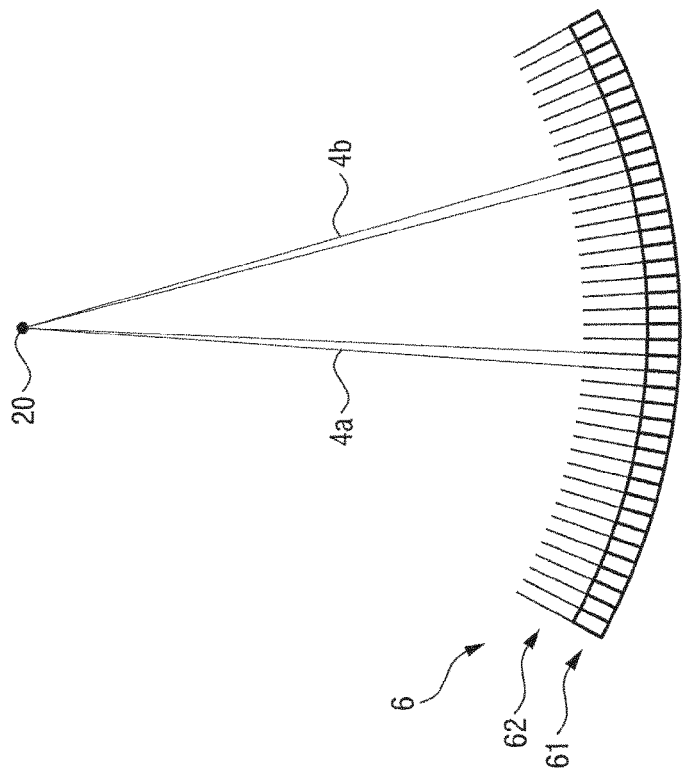
FIG.3A
FIG.3B

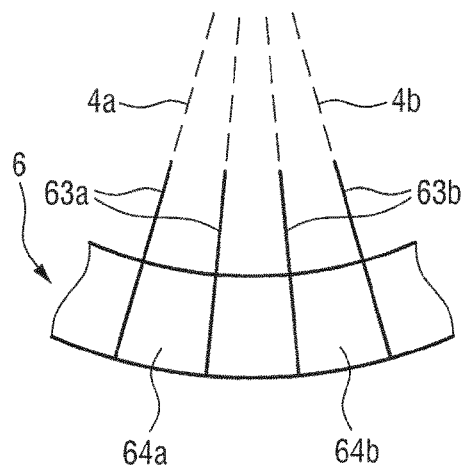
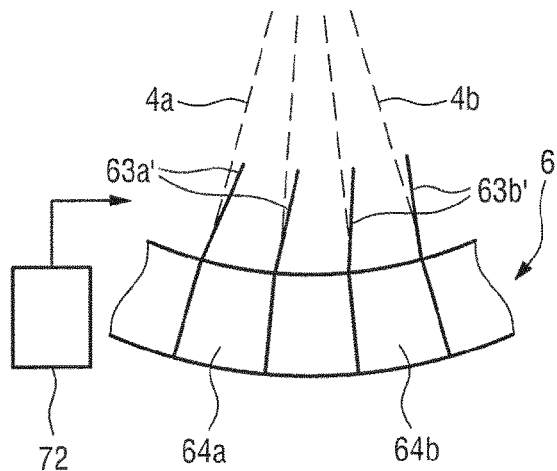
FIG.4A  FIG.4B
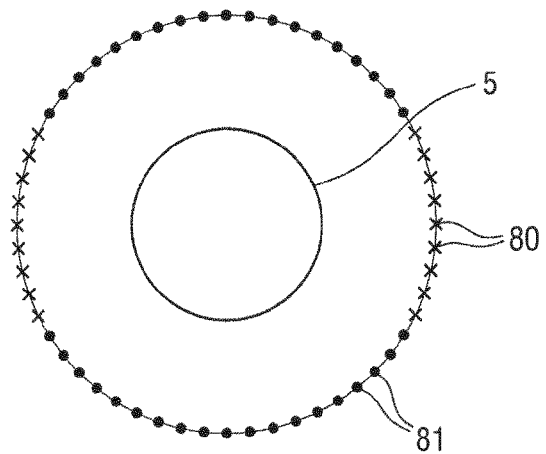
FIG.5

IMAGING APPARATUS AND METHOD

CROSS REFERENCE TO RELATED APPLICATIONS

This application is the U.S. National Phase application under 35 U.S.C. §371 of International Application No. PCT/EP2015/071734, filed Sep. 22, 2015, published as WO 2016/050562 on Apr. 7, 2016, which claims the benefit of European Patent Application Number 14187276.2 filed Oct. 1, 2014. These applications are hereby incorporated by reference herein.

FIELD OF THE INVENTION

The present invention relates to an imaging apparatus and a corresponding imaging method, in particular for CT (computed tomography).

BACKGROUND OF THE INVENTION

Photon counting CT detectors suffer from the so-called pile-up effect. In the extreme case of very high flux (i.e. radiation impinging on the detector), complete paralysis appears where the detector is fully saturated and does not output any counts at all. Unfortunately, this may happen consistently for all detector pixels which measure only a very small ray length of the radiation beam through the object of examination, e.g. a patient. In other words, all projections may be truncated, particularly on both sides where the radiation does not penetrate the object or only a thin part of the object. This type of truncated projections is quite undesired for reconstruction of images. In particular, quantitative reconstruction becomes almost impossible.

Several attempts have been made to overcome the problem of this pile-up effect and of truncated projections. For instance, WO 2013/093726 A1 discloses a detection apparatus comprising a pile-up determining unit for determining whether detection signal pulses being indicative of detected photons are caused by a pile-up event or by a non-pile-up event, wherein a detection values generating unit generates detection values depending on the detection signal pulses and depending on the determination whether the respective detection signal pulse is caused by a pile-up event or by a non-pile-up event. The detection signal pulse if caused by pile-up events may be rejected while generating the detection values. This allows for an improved quality of the generated detection values.

SUMMARY OF THE INVENTION

It is an object of the present invention to provide an imaging apparatus and a corresponding imaging method providing an alternative solution for overcoming the problems resulting from the pile-up effect and truncated projections.

In a first aspect of the present invention an imaging apparatus is presented comprising:

a radiation source for emitting radiation from a focal region through an imaging area, a detection unit for detecting radiation from said imaging area, said detection unit comprising an anti-scatter grid and a detector, a gantry to which said radiation source and said detection unit are mounted and which allows rotation of said radiation source and said detection unit around said imaging area, and a controller for controlling said detection unit to detect radiation at a plurality of projection positions during rotation around said imaging area and for manipulating the position, setting and/or orientation of at least a part of said radiation source and/or said detection unit at first projection positions so that the radiation incident on the detector at said first projection positions is attenuated by said anti-scatter grid to a larger extent compared to second projection positions representing the remaining projection positions.

In a further aspect of the present invention, a corresponding imaging method is presented comprising:

emitting radiation from a focal region through an imaging area by a radiation source, detecting radiation from said imaging area by a detection unit comprising an anti-scatter grid and a detector, rotating said radiation source and said detection unit around said imaging area during radiation emission and detection, and controlling said detection unit to detect radiation at a plurality of projection positions during rotation around said imaging area and for manipulating the position, setting and/or orientation of at least a part of said radiation source and/or said detection unit at first projection positions so that the radiation incident on the detector at said first projection positions is attenuated by said anti-scatter grid to a larger extent compared to second projection positions representing the remaining projection positions.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method has similar and/or identical preferred embodiments as the claimed device and as defined in the dependent claims.

The present invention is based on the idea to reduce the flux that hits the detector once in a while, i.e. at a certain number of projection positions of all the projection positions at which radiation is detected around the imaging area in which the object of examination is arranged, which projection positions are distributed around the imaging area. In this context, the term "projection position" shall be understood as corresponding to gantry position, gantry angle or projection angle, i.e. the angular position of the radiation source and the detection unit at which radiation is detected. The reduction of the primary flux (i.e. of the intensity of the primary radiation reaching the detector) is achieved according to the present invention by manipulating the position, setting and/or orientation of at least a part of the radiation source and/or the detection unit such that the anti-scatter grid, which is generally provided for suppressing scattered radiation only so that the detector pixels are completely illuminated by the radiation incident from the imaging area, provide an additional attenuation of said radiation. In other words, at said first projection positions, the anti-scatter grid provides for a partly shadowing of the detector, in particular of each detector pixel, to reduce the primary flux at each detector pixel to avoid the pile-up effect in said detector pixels. This reduction of the flux will facilitates an accurate measurement of the complete projections, i.e. the reduced flux does not (or at least to a lower extent) lead to a pile-up effect in the detector pixels at the first projection positions.

It should be noted that "first projection position" shall be understood as a projection position at which a projection is acquired with a setting of the position and/or orientation of said radiation source and/or said detection unit, i.e. relative to each other, which is different from the setting of said parameters used at said "second projection positions". At the second projection positions standard (nominal) settings are used as in conventional scanning, whereby generally the settings are identical for all second projection positions. At the first projection positions settings different from the settings at the second projection positions are used, whereby at all first projection positions the same settings can be used or different settings can be used for each single first projection positions or groups of projection positions.

In an embodiment, said projection positions are distributed around said imaging area. For instance, the first projection positions are equally distributed around said imaging area or are arranged according to the position, orientation and/or size of the object of examination. In other words, in one embodiment the first projection positions are preferably not arranged adjacent to each other in angular direction, but between subsequent first projection positions. At second projection positions the radiation source and/or the detection unit are positioned and/or oriented such that the anti-scatter grid does not lead to an additional shadowing of the detector elements (i.e. to an additional attenuation of the incident radiation), but the full radiation is impinging under respective detector elements. This improves the quality of reconstructed images, which are reconstructed from the radiation detected at first and second projection positions. In another embodiment at a certain larger angular range only first projection positions are arranged since the projection positions at this angular range the undesired pile-up effect may appear, e.g. due to the position of patient, which may be such that primary radiation directly hits the detector and does not go through the patient at the side areas of the detector.

In another embodiment said controller is configured to control said radiation source and/or said detection unit to change their position and/or orientation relative to each other at first projection positions during the rotation around said imaging area. For instance if the projections are taken directly from above and underneath the patient, all the emitted radiation may go through the patient and is hence attenuated by the patient. But if projections are taken from the side of the patient, part of the radiation (above and below the patient) may directly hit the detector since is does not go through the patient. Hence, in this angular ranges the position and/or orientation of the radiation source and the detection unit, or at least a part thereof, relative to each other may be manipulated to have first projection positions in these angular ranges to obtain the above explained (artificial) shadowing there, whereas in the remaining angular ranges second projection positions are arranged.

In a further embodiment this control may even be made more adaptive so that the amount of manipulation of the relative orientation and/or position and/or setting may be changed continuously or multiple times during one rotation. For instance, comparing a projection from a left side of the patient and from a right side of the patient, the manipulation may even be made in the opposition direction.

Preferably, calibration measurements made in advance for different manipulations of the position, setting and/or orientation of at least a part of the radiation source and/or the detection unit to find out to which extent the radiation is attenuated that reaches the different detector elements since, depending on the design of the radiation source and the detection unit the detection elements may be unequally shadowed along the complete detector. These calibration measurements may then be used in a reconstruction process to correct the detected radiation at first projection positions.

For achieving the manipulation of the position, setting and/or orientation of at least a part of the radiation source and/or the detection unit various options exist which may be used separately or in arbitrary combination.

In one embodiment, the controller is configured to control said radiation source, or at least a part thereof, to change its relative position and/or orientation with respect to the detection unit at said first projection positions compared to said second projection positions. In other words, at said second projection positions, the radiation source is at its "nominal" (or "standard") position and orientation with respect to the detection unit, whereas at the first projection positions this "nominal" position and orientation is no longer given but is changed to a certain extent on purpose to achieve the desired shadowing of the detector elements.

In another embodiment, the controller is configured to control said radiation source to change its focal spot with respect to the detector at said first projection positions compared to said second projection positions. In particular, the position of the focal spot in a trans-axial plane through the focal spot may be changed. The focal spot position may be identical for all first projection positions or may even be varied among the first projection positions, e.g. adapted based on parameters of the object of examination, such as the position of the object as will be explained below. This provides a simple measure to achieve the desired shadowing at the first projection positions by just changing a setting (e.g. of the focusing unit) of the radiation source or a manipulation of the position and/or orientation of a part (e.g. the focusing unit) of the radiation source. Radiation sources having a variable and controllable focal spot are generally known in the art, for instance from WO 2010/133920 A1, which change of the focal spot may e.g. be obtained by appropriate electron optics. The change in the focal spot may be a few mm to a few cm. The corresponding changes in intensity may thus be several 10%.

In still another embodiment, the controller is configured to control said detection unit, or at least a part thereof, to change its relative position and/or orientation with respect to the radiation source at said first projection positions compared to said second projection positions. Hence, rather than manipulating the radiation source, the detection unit, or at least a part thereof, is manipulated in this embodiment. Ways for manipulating the position and/or orientation of the detection unit are generally known in the art. For instance, WO 2010/133920 A1 describes the tilting of the anti-scatter grid which may be used as one possible means for achieving the desired change of the position, setting and/or orientation of at least a part of the detection unit. Hence, in particular implementations only the anti-scatter grid (i.e. a part of the detection unit), only the detector or both elements may be controlled to change their relative position and/or orientation with respect to the radiation source. For instance, the complete detection unit may be shifted to a certain extent in the direction of the rotation around the imaging area.

This change of the position, setting and/or orientation of the detection unit, or at least a part thereof, may be achieved, in an embodiment, by controlling said anti-scatter grid to change the angle of its lamellae at said first projection positions compared to said second projection positions. Hence, while the lamellae are in the "nominal" position when the radiation source and the detection unit are at said second projection positions in order to just suppress scattered radiation only, they are inclined differently with respect to the focal spot of the radiation source so that they provide the desired shadowing of the detection elements. The lamellae are thus tiltable at least to a certain extent in this embodiment.

In another embodiment, an actuator is provided for manipulating the relative position and/or orientation of the radiation source with respect to the detection unit and/or for manipulating the relative position and/or orientation of the detection unit with respect to the radiation source. Such an actuator may be realized in an arbitrary way, for instance by a motor, piezo-element or any other suitable means.

In still another embodiment, the imaging apparatus comprises a reconstruction unit for reconstructing an image from the detected radiation. Such a reconstruction from detected radiation is generally known in the art and shall not be described here in more detail.

Preferably, said reconstruction unit is configured to use the radiation detected at said first projection positions for data extrapolation of truncated projections obtained from radiation detected at second projection positions. Truncated projections are a commonly known problem in CT. For this reason the present invention is seeking to avoid it by avoiding detector paralysis altogether. In case truncated projections are unavoidable, but the degree of truncation moderate, the projections can be completed (for the cases of <20% truncation) with reasonable imaging results. The advantages are fewer image artifacts and also less noise because the detectors, when subjected to large amounts of pile-up, decrease in DQE (detective quantum efficiency). If the primary flux is reduced DQE goes up as well in spite of fewer photons hitting the detector. This will translate to less noise in the reconstructed image.

This finally provides for an improved accuracy of the reconstructed images.

Preferably, said controller is configured to manipulate the position, setting and/or orientation of at least a part of said radiation source and/or said detection unit at first projection positions, which amount to more than 0.1% and less than 50%, in particular more than 1% and less than 25%, of all projection positions.

In another preferred embodiment said controller is configured to manipulate the position, setting and/or orientation of at least a part of said radiation source and/or said detection unit at first projection positions depending on the position of the object of examination within the imaging area. Thus, the position of the object of examination (e.g. a patient) is preferably obtained in advance, e.g. by use of an initial scout scan or by use of other position determining means.

Further, in an embodiment said controller is configured to manipulate the position, setting and/or orientation of at least a part of said radiation source and/or said detection unit at first projection positions such that radiation incident on areas of the detector with the highest radiation flux at said second projection positions are attenuated most by said anti-scatter grid.

BRIEF DESCRIPTION OF THE DRAWINGS

These and other aspects of the invention will be apparent from and elucidated with reference to the embodiments described hereinafter. In the following drawings FIG. 2 shows a positioning of a radiation source with respect to the detection unit at a second projection position (FIG. 2A) and a first projection position (FIG. 2B), FIG. 3 shows the positioning of the detection unit with respect to the radiation source at a second projection position (FIG. 3A) and a first projection position (FIG. 3B), FIG. 4 shows the change of the inclination of the lamellae of the anti-scatter grid between a second projection position (FIG. 4A) and a first projection position (FIG. 4B), FIG. 5 shows an example of the distribution of the first and second projection positions around the imaging area.

DETAILED DESCRIPTION OF THE INVENTION

Figure 1:
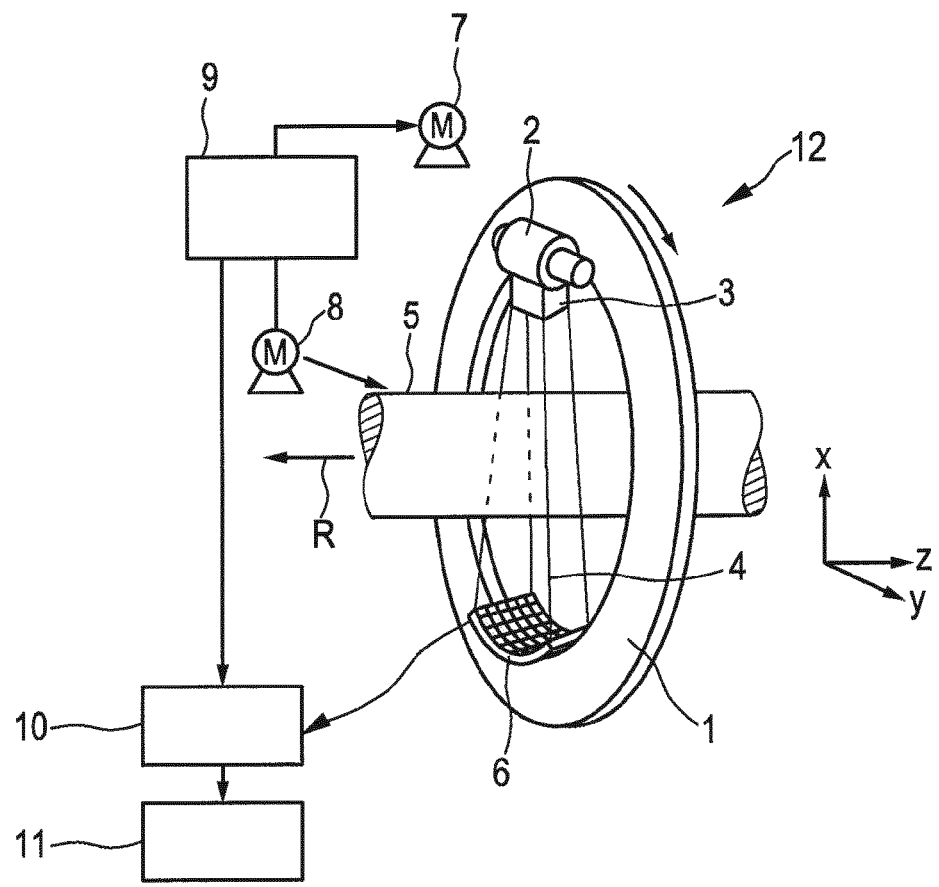
FIG. 1 shows a schematic diagram of an imaging apparatus according to the present invention.

FIG. 1 shows schematically and exemplarily an imaging apparatus 12 according to the present invention for imaging an object, in this example being a computed tomography (CT) apparatus. The CT apparatus 12 includes a gantry 1, which is capable of rotation about a rotational axis R, which extends parallel to a z direction. A radiation source 2 (also called photon source), which is, in this embodiment, a polychromatic x-ray tube, is mounted on the gantry 1. The radiation source 2 is provided with a collimator 3, which forms, in this embodiment, a conical radiation beam 4 from the radiation (photons) generated by the radiation source 2. The radiation traverses an object of examination, such as a patient, arranged in an imaging area 5 (also called examination zone), which is, in this embodiment, cylindrical. After having traversed the imaging area 5, the radiation beam 4 is incident on a detection unit 6, which comprises a two-dimensional detection surface. The detection unit 6 is also mounted on the gantry 1.

The CT apparatus 12 comprises two motors 7, 8. The gantry 1 is driven at a preferably constant but adjustable angular speed by the motor 7. The motor 8 is provided for displacing the object, for example, a patient, who is arranged on a patient table in the imaging area 5, parallel to the direction of the rotational axis R or the z axis. These motors 7, 8 are controlled by a control unit 9, for instance, such that the radiation source 2, the detection unit 6 and the imaging area 5 move relative to each other along a helical directory. However, it is also possible that the object is not moved, but that only the radiation source 2 and the detection unit 6 are rotated, i.e. that the radiation source 2 moves along a circular trajectory relative to the object or the imaging area 5. Furthermore, in another embodiment, the collimator 3 can be adapted for forming another beam shape, in particular a fan beam, and the detection unit 6 can comprise a detection surface, which is shaped corresponding to the other beam shape, in particular to the fan beam.

During a relative movement of the radiation source 2 and the imaging area 5, the detection unit 6 generates detection values (preferably one detection value per pixel, i.e. per detection element of a preferably two-dimensional array of detection elements) depending on the radiation incident on the detection surface of the detection unit 6. The detection values are preferably provided to a reconstruction unit 10 for reconstructing an image of the object based on the detection values. The image reconstructed by the reconstruction unit 10 may be provided to a display unit 11 for displaying the reconstructed image. The control unit 9 is preferentially also adapted to control the radiation source 2, the detection unit 6 and the reconstruction unit 10.

According to the present invention, the detection unit 6 comprises a detector 61 and an anti-scatter grid 62, preferably comprising a plurality of lamellae 63, as depicted in FIG. 2A. The anti-scatter grid is generally provided to suppress scattered radiation to make sure that only the primary radiation (primary flux) is incident on the detector elements 64 of the detector 61. Further, the control unit 9 is configured to control said detection unit 6 to detect radiation at a plurality of projection positions during rotation around said imaging area and for manipulating the position, setting and/or orientation of at least a part of said radiation source 2 and/or said detection unit 6 at first projection positions (or gantry position, gantry angle or projection angle) so that the radiation incident on the detector 61 at said first projection positions is attenuated by said anti-scatter grid 62 to a larger extent compared to second projection positions representing the remaining projection positions.

A first embodiment for illustrating this control is schematically depicted in FIG. 2. FIG. 2A shows the position of the focal spot 20 of the radiation source 2 at a second projection position and FIG. 2B shows the position of the focal spot, indicated in this figure by 20', at a first projection position. FIG. 2A shows two exemplary radiation beams 4a, 4b emitted from the focal spot 20 of the radiation source 2 and leading, after penetrating through the imaging area, to a corresponding detection element 64a, 64b through a respective pair of lamellae 63a, 63b of the anti-scatter grid 62. As shown in FIG. 2A, illustrating the "standard" position of the focal spot 20 of the radiation source with respect to the detection unit 6, the detector elements 64 are completely illuminated and the anti-scatter grid 62 suppresses scattered radiation only but does not attenuate the primary flux of the radiation beams 4a, 4b.

FIG. 2B shows another situation in which the focal spot, indicated by 20', is deflected with respect to the "standard" position or setting (indicated by 20 for comparison). The radiation beams 4a', 4b' do now no longer directly hit the respective detection elements 64a, 64b, but at least partly hit the lamellae 63a, 63b which thus partly shadows the detector elements 64a, 64b, i.e. the primary flux of the radiation beam, 4a', 4b' finally impinging on the detector elements 64a, 64b, is reduced compared to the situation depicted in FIG. 2A.

An actuator (not shown) may be provided in this embodiment for mechanically changing the position of the focal spot (i.e. by changing the position of a part of the radiation source), or the focal spot may be electronically shifted (i.e. a setting of the radiation source may be changed). In other embodiments the position of the (complete) radiation source 2 may be slightly changed, e.g. by the motor 7 or a separate motor (not shown) for moving the radiation source with respect to the gantry 1.

Preferably, in an embodiment the focal spot is shifted in the first projection positions depending on the position of the object of examination within the imaging area 5. The position of the object is e.g. obtained in advance by use of an initial scout scan from which the position can be estimated rather well. For instance, if patient is lying on the patient table not exactly in the middle but closer to the left edge of the patient table, part of the primary radiation is directly hitting the detector area 61a on the right hand side (in FIG. 2) of the detector 61 without penetrating the patient, i.e. that there is a large radiation flux. Thus, the described pile-up is likely to happen at the detector elements within this area 61a. In this case it is useful to shift the focal spot, as shown in FIG. 2B, to the right hand side which has the effect that radiation incident on the detector elements on the right hand side of the detector 61 (i.e. in particular in area 61a) is attenuated by said anti-scatter grid 62 to a larger extent than radiation incident on the detector elements on the left hand side of the detector 61 (i.e. in particular in area 61b). Thus, the pile-up effect is effectively reduced or completely avoided.

Thus, the amount of the shift of the focal spot can generally be used to control the area and the amount of attenuation of radiation (i.e. the area and amount of shadowing). For this purpose initial calibration measurements as mentioned above may be used as well.

Further, when the focal spot is changed, an often used bow tie filter comprising very steep edges will have a significant influence on the flux changes as well. The bow tie filter could be moved as well in this context.

FIG. 3 illustrates another embodiment in which the position, setting and/or orientation of the radiation source 2 is not manipulated for first projection positions compared to second projection positions, but the position, setting and/or orientation of the detection unit 6 is manipulated. FIG. 3A illustrates the "standard" position as already shown in FIG. 2A, and FIG. 3B shows the manipulated position of the detection unit 6. As indicated by arrow 70, the (complete) detection unit 6 is, compared to the standard position, tilted around an axis that is perpendicular to the plane of the drawing. This has the effect that the detection elements 64 of the detector 61 are shadowed compared to the situation shown in FIG. 3A leading to the desired reduction of primary flux.

In other embodiments (not shown), the (complete) detection unit 6 may be shifted in a translational direction (e.g. in a horizontal direction or in a direction along the axis perpendicular to the plane of the drawing) or in the rotational direction (i.e. around the axis or rotation around the imaging area) leading to substantially the same technical effect of shadowing the detection elements. In still other embodiments, two or more manipulations in one or more directions and/or along one or more axes of the position and/or orientation of the detection unit 6 may be provided for this purpose.

An actuator 71 may be provided in this embodiment for mechanically changing the position and/or orientation of the detection unit 6 or even only of the detector 61. In other embodiments the position of the detection unit 6 (or the detector 61) may be slightly changed, e.g. by the motor 7 or a separate motor (not shown), e.g. by moving the detection unit 6 with respect to the gantry 1.

FIG. 4 illustrates another embodiment according to the present invention. This figure shows a small part of a detector unit in which the lamellae of the anti-scatter grid 62 can be manipulated to change their inclination with respect to incident radiation. FIG. 4A shows the "standard" position of the lamellae, illustrated by exemplary lamellae 63a, 63b, so that the incident radiation 4a, 4b hits the detector elements 64a, 64b at second projection positions. FIG. 4B shows the manipulated position for detection of radiation at the first projection positions, whereby the inclination of the lamellae, indicated by reference sign 63a', 63b' are now arranged at a different angle compared to the radiation beams 4a, 4b. This has again the technical effect that the detection elements 64a, 64b are partly shadowed so that the primary flux impinging on the detection elements is reduced compared to a situation shown in FIG. 4A.

An actuator 72 may be provided in this embodiment for mechanically changing the inclination of the lamellae, e.g. piezo elements or small motors.

FIG. 5 schematically illustrates an example of the distribution of first and second projection positions around the imaging area 5. The first projection positions 80 are indicated by "x", and the second projection positions 81 are indicated by "o". In practical situations, more than 0.1% and less than 50%, or more than 1% and less than 25%, of all projection positions are first projection positions.

There may be even more first and/or second angular ranges, e.g. depending on the size, position and/or orientation of the object of examination within the imaging area. This information may e.g. be obtained in an initial scout scan or any other detection unit (e.g. an imaging unit using an object detection algorithm), or may even be entered by a user, e.g. an operator of the device or a nurse. This information may then be used to provide an even more precise control of the locations of the first projections positions and of the amount of manipulation of the position and/or radiation of the radiation source and the detection unit relative to each other at first projection positions.

For instance, generally for each angular position around the imaging area 5 it may be determined if it is a first or second projection position and, if it is a first projection position, to which extent a manipulation of position and/or orientation of the radiation source and the detection unit relative to each other shall be made to obtain the desired shadowing. Hence, generally for each first position a different manipulation (or setting) of the position and/or orientation of the radiation source and the detection unit relative to each other can be used. Such fast changes are e.g. possible with electron focusing optics by which the focal spot of the radiation source can be changed from one angular position to the next angular position. In a less precise embodiment such a control may only be made after a number x of projection positions, x being e.g. in the range from 2 to 500, or the manipulation may be identical for all first projection positions.

It shall be understood that the number of first and second projection positions and the percentage of their distribution as well as their distribution around the imaging area 5 is to be understood as an example only. Many other implementations are possible, and the total number shown in FIG. 5 does also not show a realistic example, but represents a simplified example that is only provided for illustrative purposes of the distribution.

Figure 6:
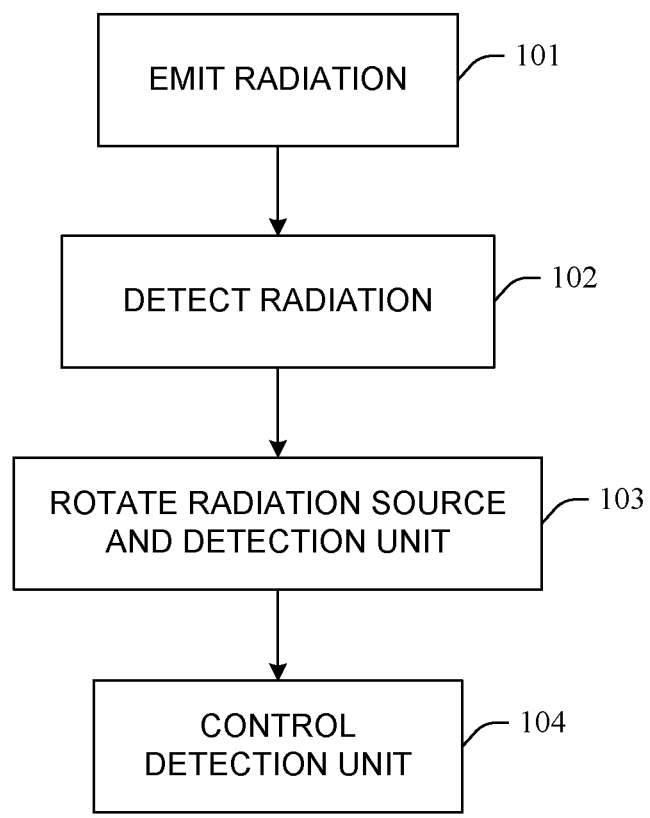
FIG. 6 shows a flow chart of an imaging method according to the present invention.

FIG. 6 shows a flow chart of an imaging method according to the present invention. In a first step 101, radiation is emitted from a focal region (focal spot) through an imaging area by a radiation source. In a second step 102, radiation is detected from said imaging area by a detection unit comprising an anti-scatter grid and a detector. In a third step 103, said radiation source and said detection unit are rotated around said imaging area during radiation emission and detection. In a fourth step 104, said detection unit is controlled to detect radiation at a plurality of projection positions during rotation around said imaging area and to manipulate the position, setting and/or orientation of at least a part of said radiation source and/or said detection unit at first projection positions so that the radiation incident on the detector at said first projection position is attenuated by said anti-scatter grid to a larger extent compared to second projection positions representing the remaining projection positions. It is clear that further embodiments of the imaging method exist that substantially correspond to the above explained embodiments of the imaging apparatus according to the present invention.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Imaging apparatus comprising:
   a radiation source for emitting radiation from a focal region through an imaging area,
   a detection unit for detecting radiation from said imaging area, said detection unit comprising an anti-scatter grid and a detector,
   a gantry to which said radiation source and said detection unit are mounted and which allows rotation of said radiation source and said detection unit around said imaging area, and
   a controller for controlling said detection unit to detect radiation at a plurality of projection positions during rotation around said imaging area and for manipulating the position, setting and/or orientation of at least a part of said radiation source and/or said detection unit at first projection positions so that the radiation incident on the detector at said first projection positions is attenuated by said anti-scatter grid to a larger extent compared to second projection positions representing the remaining projection positions.

2. Imaging apparatus as claimed in claim 1, wherein said first projection positions are distributed around said imaging area.

3. Imaging apparatus as claimed in claim 1, wherein said controller is configured to control said radiation source and/or said detection unit, or at least a part thereof, to change their position and/or orientation relative to each other at first projection positions during the rotation around said imaging area.

4. Imaging apparatus as claimed in claim 1, wherein said controller is configured to control said radiation source, or at least a part thereof, to change its relative position and/or orientation with respect to the detection unit at said first projection positions compared to said second projection positions.

5. Imaging apparatus as claimed in claim 1, wherein said controller is configured to control said radiation source to change its focal spot with respect to the detector at said first projection positions compared to said second projection positions.

6. Imaging apparatus as claimed in claim 1, wherein said controller is configured to control said detection unit, or at least a part thereof, to change its relative position and/or orientation with respect to the radiation source at said first projection positions compared to said second projection positions.

7. Imaging apparatus as claimed in claim 1,
wherein said controller is configured to control said anti-scatter grid to change the angle of its lamellae at said first projection positions compared to said second projection positions.

8. Imaging apparatus as claimed in claim 1,
further comprising an actuator for manipulating the relative position and/or orientation of the radiation source, or at least a part thereof, with respect to the detection unit and/or for manipulating the relative position and/or orientation of the detection unit, or at least a part thereof, with respect to the radiation source.

9. Imaging apparatus as claimed in claim 1,
further comprising a reconstruction unit for reconstructing an image from the detected radiation.

10. Imaging apparatus as claimed in claim 9,
wherein said reconstruction unit is configured to use the radiation detected at said first projection positions for data extrapolation of truncated projections obtained from radiation detected at said second projection positions.

11. Imaging apparatus as claimed in claim 1,
wherein said controller is configured to manipulate the position, setting and/or orientation of at least a part of said radiation source and/or said detection unit at said first projection positions, which amount to more than 0.1% and less than 50% of all projection positions.

12. Imaging apparatus as claimed in claim 1,
wherein said controller is configured to manipulate the position, setting and/or orientation of at least a part of said radiation source and/or said detection unit at said first projection positions depending on a position of an object of examination within the imaging area.

13. Imaging apparatus as claimed in claim 1,
wherein said controller is configured to manipulate the position, setting and/or orientation of at least a part of said radiation source and/or said detection unit at said first projection positions such that radiation incident on areas of the detector with the highest radiation flux at said second projection positions are attenuated most by said anti-scatter grid.

14. Imaging method comprising:
emitting radiation from a focal region through an imaging area by a radiation source,
detecting radiation from said imaging area by a detection unit comprising an anti-scatter grid and a detector,
rotating said radiation source and said detection unit around said imaging area during radiation emission and detection,
controlling, with a controller, said detection unit to detect radiation at a plurality of projection positions during rotation around said imaging area, and
manipulating, with said controller, the position, setting and/or orientation of at least a part of said radiation source and/or said detection unit at first projection positions so that the radiation incident on the detector at said first projection positions is attenuated by said anti-scatter grid to a larger extent compared to second projection positions representing the remaining projection positions.

15. A non-transitory computer program comprising program code means for causing a computer to control an imaging apparatus, to carry out the steps of the method as claimed in claim 14 when said computer program is carried out on the computer.

* * * * *